(12) United States Patent
Hirai et al.

(10) Patent No.: US 11,179,333 B2
(45) Date of Patent: Nov. 23, 2021

(54) EMULSION COMPOSITION

(71) Applicant: FUJI CHEMICAL INDUSTRIES CO., LTD., Nakaniikawa-gun (JP)

(72) Inventors: Katsuyuki Hirai, Nakaniikawa-gun (JP); Yuichiro Yamagishi, Nakaniikawa-gun (JP); Nobuko Hongo, Nakaniikawa-gun (JP); Jiro Takahashi, Nakaniikawa-gun (JP); Rina Sakaguchi, Nakaniikawa-gun (JP); Akitoshi Kitamura, Nakaniikawa-gun (JP)

(73) Assignee: FUJI CHEMICAL INDUSTRIES CO., LTD., Nakaniikawa-gun (JP)

( * ) Notice: Subject to any disclaimer, the term of this patent is extended or adjusted under 35 U.S.C. 154(b) by 0 days.

(21) Appl. No.: 15/305,791

(22) PCT Filed: Aug. 28, 2015

(86) PCT No.: PCT/JP2015/074359
§ 371 (c)(1),
(2) Date: Oct. 21, 2016

(87) PCT Pub. No.: WO2016/031954
PCT Pub. Date: Mar. 3, 2016

(65) Prior Publication Data
US 2017/0042808 A1 Feb. 16, 2017

(30) Foreign Application Priority Data

Aug. 29, 2014 (JP) .............................. JP2014-175540
Oct. 27, 2014 (JP) .............................. JP2014-218699
Oct. 30, 2014 (JP) .............................. JP2014-221027

(51) Int. Cl.
| | |
|---|---|
| A61K 9/107 | (2006.01) |
| A61K 47/10 | (2017.01) |
| A61K 47/14 | (2017.01) |
| A61K 47/24 | (2006.01) |
| A61K 31/015 | (2006.01) |
| A61K 31/122 | (2006.01) |
| A61K 31/065 | (2006.01) |
| A61K 9/00 | (2006.01) |
| A61K 47/26 | (2006.01) |
| A61K 9/48 | (2006.01) |
| A61K 31/685 | (2006.01) |
| A61K 31/047 | (2006.01) |
| A61K 9/06 | (2006.01) |
| A61K 31/22 | (2006.01) |

(52) U.S. Cl.
CPC ............ *A61K 9/107* (2013.01); *A61K 9/0014* (2013.01); *A61K 9/0053* (2013.01); *A61K 9/0095* (2013.01); *A61K 9/06* (2013.01); *A61K 9/48* (2013.01); *A61K 9/4858* (2013.01); *A61K 31/015* (2013.01); *A61K 31/047* (2013.01); *A61K 31/065* (2013.01); *A61K 31/122* (2013.01); *A61K 31/22* (2013.01); *A61K 31/685* (2013.01); *A61K 47/10* (2013.01); *A61K 47/14* (2013.01); *A61K 47/24* (2013.01); *A61K 47/26* (2013.01)

(58) Field of Classification Search
CPC ...... A61K 9/0014; A61K 9/0095; A61K 9/06; A61K 9/4858; A61K 9/107; A61K 31/122; A61K 47/26; A61K 47/24; A61K 47/14
See application file for complete search history.

(56) References Cited

U.S. PATENT DOCUMENTS

| | | | |
|---|---|---|---|
| 2007/0286930 A1 | 12/2007 | Ogawa et al. | |
| 2008/0131515 A1 | 6/2008 | Ogawa et al. | |

FOREIGN PATENT DOCUMENTS

| | | |
|---|---|---|
| JP | 2008-13751 A | 1/2008 |
| JP | 2008-154577 A | 7/2008 |
| JP | 2008-280257 A | 11/2008 |
| JP | 2011-92083 A | 5/2011 |
| WO | 2005/065652 | 7/2005 |
| WO | 2008/140065 A2 | 11/2008 |
| WO | 2014/054651 | 4/2014 |

OTHER PUBLICATIONS

"Sucrose esters of fatty acids DK Ester", Dai-Ichi Kogyo Seiyaku Co, http://www.mjc.biz.id/uploads/6/2/5/9/62591723/dk_ester_brochure.pdf, accessed Jun. 8, 2020 (Year: 2020).*
"Ryoto Sugar Ester", Mitsubishi-Chemical Foods Corporation, https://www.mfc.co.jp/english/ryoto_se/seihin.htm, accessed Jun. 8, 2020 (Year: 2020).*
International Search Report dated Oct. 6, 2015 in PCT/JP2015/074359 filed Aug. 28, 2015.
Extended European Search Report as received in the corresponding European Patent Application No. 15836804.3-1114 / 3187181 dated Jan. 10, 2018, 7 pages.

* cited by examiner

*Primary Examiner* — Melissa L Fisher
(74) *Attorney, Agent, or Firm* — Oblon, McClelland, Maier & Neustadt, L.L.P.

(57) ABSTRACT

Provided is an emulsion composition that allows a lipophilic ingredient to have high stability and high in vivo absorbability.
The emulsion composition includes (a) a lipophilic ingredient, (b) a phospholipid, (c) a polyol, (d) water, (e) a sucrose fatty acid ester, and (f) a polyglycerol fatty acid ester. The content of the phospholipid (b) is from 2.0 to 15.0 parts by weight to 100 parts by weight of the total of the emulsion composition, and the weight ratio of the (f) polyglycerol fatty acid ester to the (e) sucrose fatty acid ester is from 0.1 to 0.9 parts by weight of the (f) polyglycerol fatty acid ester to 1 part by weight of the (e) sucrose fatty acid ester.

6 Claims, 2 Drawing Sheets

EMULSION COMPOSITION

TECHNICAL FIELD

The present invention relates to an emulsion composition containing a lipophilic ingredient with a high level of stability and in vivo absorbability. More specifically, the present invention relates to an emulsion composition containing a lipophilic ingredient such as astaxanthin in such a state that the lipophilic ingredient is stable and has high in vivo absorbability, and also relates to a food or beverage product, a pharmaceutical product, and/or a cosmetic product containing such an emulsion composition.

BACKGROUND ART

Lipophilic ingredients are conventionally added to aqueous beverages, aqueous food products, aqueous cosmetics, and other products. However, since lipophilic ingredients are generally slightly soluble in water, they are generally dispersed by emulsification or the like.

For example, a known emulsion composition with high emulsion stability includes a lipophilic ingredient, a sucrose fatty acid ester, a polyglycerol fatty acid ester, a phospholipid, a polyol, and water (Patent Literature 1).

Another known emulsion composition containing astaxanthin and/or an ester thereof has a particle size of from 5 to 100 nm and includes an aqueous phase containing at least one water-soluble emulsifying agent; and an oil phase containing tocopherol, lecithin, and from 0.1 to 10% by weight of astaxanthin and/or an ester thereof to the weight of the composition, where the water-soluble emulsifying agent is selected from the group consisting of a sucrose fatty acid ester, a polyglycerol fatty acid ester, and a sorbitan fatty acid ester (Patent Literature 2).

A further known emulsion composition contains a phospholipid, an oily ingredient, and a surfactant, where the content of the surfactant is 0.5 times more than the content of the oily ingredient and 5 times more than the content of the phospholipid (Patent Literature 3).

Carotenoids such as astaxanthin, which is one of lipophilic ingredients, are known to have low in vivo absorbability. Carotenoids such as astaxanthin have a high manufacturing cost and thus a high retail price. Therefore, studies have been conducted on a variety of methods for allowing it to be efficiently absorbed in vivo. However, those are not satisfactory enough.

CITATION LIST

Patent Literatures

Patent Literature 1: JP 2011-92083 A
Patent Literature 2: JP 2008-13751 A
Patent Literature 3: JP 2008-154577 A

SUMMARY OF INVENTION

Technical Problem

An object of the present invention is to provide an emulsion composition, in which a lipophilic ingredient has high stability, the lipophilic ingredient achieves high in vivo absorbability, and a large amount of the lipophilic ingredient can be contained.

Solution to Problem

As a result of intensive studies, the inventors have accomplished the present invention based on findings that the problem can be solved when the ingredients described below are used to form an emulsion composition and the content of each ingredient is controlled to fall within a predetermined range. Specifically, the present invention is directed to the following.

[1] An emulsion composition containing (a) a lipophilic ingredient, (b) a phospholipid, (c) a polyol, (d) water, (e) a sucrose fatty acid ester, and (f) a polyglycerol fatty acid ester, where the content of the phospholipid (b) is from 2.0 to 15.0 parts by weight to 100 parts by weight of the total of the emulsion composition, and the weight ratio of the polyglycerol fatty acid ester (f) to the sucrose fatty acid ester (e) is from 0.1 to 0.9 parts by weight of the polyglycerol fatty acid ester (f) to 1 part by weight of the sucrose fatty acid ester (e).

[2] The emulsion composition according to [1], where the (a) lipophilic ingredient includes at least one (a-1) carotenoid and at least one (a-2) fat or oil.

[3] The emulsion composition according to [2], where the weight ratio of the (b) phospholipid to the (a-1) carotenoid is from 1.1 to 4.5 parts by weight of the phospholipid (b) to 1 part by weight of the (a-1) carotenoid.

[4] The emulsion composition according to any one of [1] to [3], where the (a-1) carotenoid is at least one selected from the group consisting of lycopene, n-carotene, γ-carotene, phytofluene, phytoene, canthaxanthin, astaxanthin, R-cryptoxanthin, capsanthin, lutein, zeaxanthin, and fatty acid esters thereof.

[5] The emulsion composition according to any one of [1] to [4], where the (a-1) carotenoid includes at least astaxanthin or a fatty acid ester thereof.

[6] The emulsion composition according to [2], where the (a-2) fat or oil includes an acylglycerol including at least one selected from the group consisting of a monoglyceride, a diglyceride, and a triglyceride.

[7] The emulsion composition according to [6], where the weight ratio of the acylglycerol to the (a-1) carotenoid is from 0.8 to 6.0 parts by weight of the acylglycerol to 1 part by weight of the (a-1) carotenoid.

[8] The emulsion composition according to any one of [1] to [7], where the (b) phospholipid includes at least one selected from the group consisting of lecithin and lysolecithin.

[9] The emulsion composition according to any one of [1] to [8], where the (c) polyol includes at least one selected from the group consisting of glycerin, diglycerin, propylene glycol, ethylene glycol, 1,3-butylene glycol, polyethylene glycol, sorbitol, mannitol, dipropylene glycol, and sorbitan.

[10] The emulsion composition according to any one of [1] to [9], where the (e) sucrose fatty acid ester includes at least one selected from the group consisting of sucrose monooleate, sucrose monostearate, sucrose monopalmitate, sucrose monomyristate, sucrose monolaurate, sucrose dioleate, sucrose distearate, sucrose dipalmitate, sucrose dimyristate, and sucrose dilaurate.

[11] The emulsion composition according to any one of [1] to [10], where the (f) polyglycerol fatty acid ester includes at least one selected from the group consisting of hexaglycerol monooleate, hexaglycerol monostearate, hexaglycerol monopalmitate, hexaglycerol monomyristate, hexaglycerol monolaurate, decaglycerol monooleate, decaglycerol monostearate, decaglycerol monopalmitate, decaglycerol monomyristate, decaglycerol monolaurate, glycerol stearate citrate, and decaglycerol distearate.

[12] The emulsion composition according to any one of [4] to [11], where the astaxanthin is a *Haematococcus alga* extract.

[13] The emulsion composition according to [12], where the *Haematococcus alga* extract has an astaxanthin content of 9% by weight or more.

[14] The emulsion composition according to any one of [1] to [13], where the content of (d) water is from 12 to 15 parts by weight and the content of the carotenoid is at least 1.5 parts by weight to 100 parts by weight of the total of the emulsion composition.

[15] The emulsion composition according to any one of [1] to [14], which is in the form of an oil-in-water emulsion.

[16] A food, pharmaceutical, and/or cosmetic product including the emulsion composition according to any one of [1] to [15].

[17] A hard or soft capsule preparation including the emulsion composition according to any one of [1] to [15].

[18] A method of preparing the emulsion composition according to any one of [1] to [15], the method including: (1) mixing and dissolving a sucrose fatty acid ester and optionally a polyol in water to form an aqueous phase; (2) mixing and dissolving a lipophilic ingredient, a polyglycerol fatty acid ester and a phospholipid, and optionally a polyol to form an oil phase; and (3) mixing the aqueous phase and the oil phase.

Advantageous Effects of Invention

The emulsion composition of the present invention can have high stability, high in vivo absorbability, and a high oil or fat content.

DESCRIPTION OF EMBODIMENTS

Figure 1:
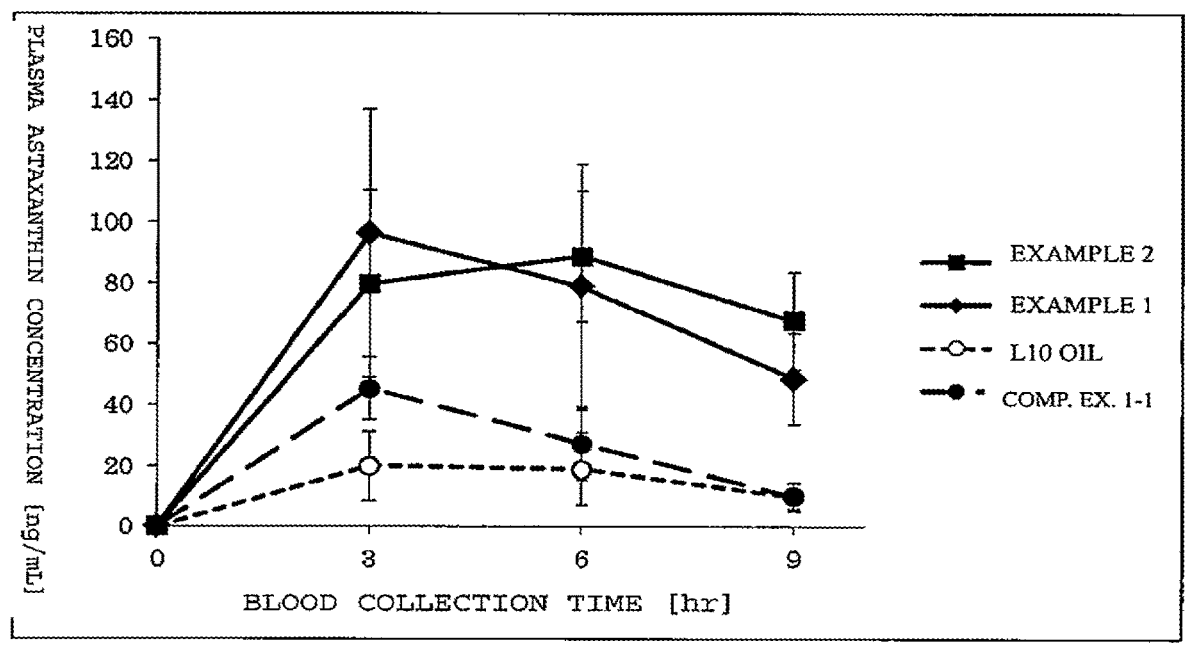
FIG. 1 illustrates the results of an oral absorbability test on rats using the emulsion composition of the present invention.

Hereinafter, the emulsion composition of the present invention will be described in detail.

The emulsion composition of the present invention includes (a) a lipophilic ingredient, (b) a phospholipid, (c) a polyol, (d) water, (e) a sucrose fatty acid ester, and (f) a polyglycerol fatty acid ester.

(a) Lipophilic Ingredient

In the emulsion composition of the present invention, the lipophilic ingredient may be of any type as long as it is insoluble or hardly soluble in water and soluble in an oily medium. For example, (a-1) a carotenoid (also called carotinoid) and (a-2) an oil or fat is preferably used as the lipophilic ingredient.

(a-1) Carotenoid

A carotenoid as an example of the lipophilic ingredient is a terpenoid pigment with a color ranging from yellow to red, examples of which include carotenoids derived from plants, algae, and bacteria. In the present invention, examples of the carotenoid include not only naturally-occurring carotenoids but also synthetic carotenoids obtained by conventional methods. For example, many of carotenes shown below as carotenoids are also synthesized, and many commercially-available products of β-carotene are synthesized.

Examples of the carotenoid include hydrocarbons (carotenes) and oxidized alcohol derivatives thereof (xanthophylls).

Examples of the carotenoid include actinioerythrol, astaxanthin, bixin, canthaxanthin, capsanthin, capsorbin, β-8'-apo-carotenal (apocarotenal), β-12'-apo-carotenal, α-carotene, β-carotene, carotene (a mixture of α- and β-carotenes), γ-carotene, β-cryptoxanthin, lutein, lycopene, violerythrin, zeaxanthin, phytoene, phytofluene, and esters (fatty acid esters) of hydroxyl- or carboxyl-containing compounds selected from the above.

Among these carotenoids, one or more selected from the group consisting of lycopene, β-carotene, γ-carotene, phytofluene, phytoene, canthaxanthin, astaxanthin, β-cryptoxanthin, capsanthin, lutein, zeaxanthin, and fatty acid esters thereof are more preferred, and one or more selected from astaxanthin and a fatty acid ester thereof are even more preferred. In this case, fatty acid esters of carotenoids or astaxanthin are preferably linear or branched, saturated or unsaturated, fatty acid esters of 8 to 22 carbon atoms.

In general, carotenoids can be extracted from plant materials. Such carotenoids have various functions. For example, lutein extracted from Marigold petals is widely used as a raw material for poultry feed, and has the function of coloring poultry skin and fat, and poultry eggs.

Carotenoids particularly preferably used in the present invention include the free form of astaxanthin and/or its derivatives such as esters of astaxanthin (hereinafter, these are generically referred to as "astaxanthins"). Astaxanthins are known to have high antioxidative effects, antioxidant effects, anti-inflammatory effects, skin antiaging effects, skin-whitening effects, and other biological effects, and also known as colorants with colors ranging from yellow to red.

Astaxanthins are red pigments having an absorption maximum at 476 nm (ethanol) or 468 nm (hexane) and belong to xanthophylls as one kind of carotenoids (Davies, B. H.: In "Chemistry and Biochemistry of Plant Pigments", T. W. Goodwin ed., 2nd ed., 38-165, Academic Press, NY, 1976). The chemical name of the free form of astaxanthin is 3,3'-dihydroxy-β,β-carotene-4, 4'-dione ($C_{40}H_{52}O_4$, molecular weight 596.82).

Astaxanthin has three isomers: 3S,3S'-form, 3S,3R'-form (meso form), and 3R,3R'-form depending on the steric configuration of the hydroxyl group at the 3(3')-position of the ring structures present at both ends of the molecule. Astaxanthin also has cis and trans geometrical isomers with respect to the conjugated double bond at the center of the molecule. Examples include the all-cis-isomer, the 9-cis isomer, and the 13-cis isomer.

The hydroxyl group at the 3(3')-position can form an ester with a fatty acid. For example, astaxanthins obtained from krill contain a relatively large amount of a diester having two fatty acids bonded thereto (Yamaguchi, K., Miki, W., Toriu, N., Kondo, Y., Murakami, M., Konosu, S., Satake, M., Fujita, T.: The composition of carotenoid pigments in the Antarctic krill *Euphausia superba*, Bull. Jap. Sos. Sci. Fish., 1983, 49, p. 1411-1415). Astaxanthin obtained from *Haematococcus pluvialis*, in which astaxanthin is in the 3S,3S'-form, contain a relatively large amount of a monoester having one fatty acid bonded thereto (Renstrom, B., Liaaen-Jensen, S.: Fatty acids of some esterified carotenols, Comp. Biochem. Physiol. B, Comp. Biochem., 1981, 69, 625-627).

Astaxanthin obtained from *Phaffia Rhodozyma* is the 3R,3R'-form (Andrewes, A. G, Starr, M. P.: (3R,3'R)-Astraxanthin from the yeast *Phaffia rhodozyma*, Phytochem., 1976, 15, p. 1009-1011), which has a structure reverse to the 3S,3S'-form generally found in nature. This is also present in the non-ester form without forming any ester with a fatty acid, in other words, in the free form (Andrewes, A. G, Phaffia, H. J., Starr, M. P.: Carotenids of *Phaffia rhodozyma*, a red pigmented fermenting yeast, Phytochem., 1976, 15, p. 1003-1007).

As regards the astaxanthins, the emulsion composition of the present invention may contain an astaxanthins-containing oil, which is separated or extracted from astaxanthins-containing natural products. Examples of such an astaxanthins-containing oil include extracts obtained from cultures of a red yeast, *Phaffia*, a green alga *Haematococcus*, marine bacteria, or other organisms; and extracts from antarctic krill or the like.

The astaxanthins that can be used in the present invention may be the extracts mentioned above, products obtained by appropriate purification of the extracts as needed, or chemically synthesized products.

In particular, the astaxanthins are preferably products extracted from a *Haematococcus* alga (*Haematococcus alga* extracts) in view of quality and productivity.

Examples of the *Haematococcus alga* as a source of *Haematococcus alga* extracts for use in the invention include *Haematococcus pluvialis, Haematococcus lacustris, Haematococcus capensis, Haematococcus droebakensis*, and *Haematococcus zimbabwiensis*.

In the present invention, various methods for culturing a *Haematococcus alga*, such as the methods disclosed in JP 8-103288 A, may be used without limitation, as long as the morphology can be changed from vegetable cells to cyst cells, which are dormant cells.

*Haematococcus alga* extracts that can be used in the present invention are obtained by crushing, as needed, the cell walls of the above raw materials, for example, by the method disclosed in JP 5-68585 A, adding, to the product, an organic solvent such as acetone, ether, chloroform, and alcohol (e.g., ethanol or methanol) or an extractant such as carbon dioxide in a supercritical state, and then performing extraction.

In the present invention, widely commercially available *Haematococcus alga* extracts may be used, examples of which include ASTOTS-S, ASTOTS-2.5 0, ASTOTS-5 0, and ASTOTS-10 0 manufactured by Takedashiki Co., Ltd.; AstaReal Oil 50F and AstaReal oil 5F manufactured by Fuji Chemical Industries Co., Ltd.; and BioAstin SCE7 manufactured by Toyo Koso Kagaku Co., Ltd. *Haematococcus alga* extracts are composed mainly of astaxanthins and acylglycerol. *Haematococcus alga* extracts are advantageous because they contain acylglycerol which belong to the oils and fats described below. *Haematococcus alga* extracts preferably have a high astaxanthin content. The astaxanthins content of the extracts is preferably 9% by weight or more, more preferably from 9 to 40% by weight, even more preferably from 18 to 30% by weight.

Methods for obtaining a high content of astaxanthins from *Haematococcus* green algae are preferably sealed culture methods, which are prevented from contamination with or growth of foreign microorganisms and less likely to suffer from contamination with other foreign matters. Suitable examples include culture methods using culture media together with a dome-shaped, conical, or cylindrical, airtight culture apparatus and a gas discharge device movable in the apparatus (see WO 99/50384); methods using an airtight culture apparatus in which a light source is provided to apply light from inside for culture; and culture methods using a flat culture vessel. The astaxanthins-containing *Haematococcus alga* may be of any type. *Haematococcus* algae having a high content of astaxanthins are preferred because the extraction efficiency increases with increasing content. For example, *Haematococcus* algae containing 0.1 to 10% of astaxanthins are preferred.

According to conventional methods, *Haematococcus alga* cells can be obtained by, for example, centrifugation or filtration of the culture medium used in the culture methods mentioned above. For example, *Haematococcus alga* cells may be used in a wet state when subjected to crushing (in this case, the amount of the cells used is calculated on a dry basis), or *Haematococcus alga* cells separated by filtration may be suspended together with an antioxidant in water and then dried by spray drying before use.

Examples of chemically synthesized astaxanthin include AstaSana available from DSM and Lucantin Pink available from BASF.

As regards the content of astaxanthins, the content of the free form of astaxanthin is calculated directly, but the content of a fatty acid ester of astaxanthin is calculated in terms of the free form of astaxanthin.

(a-2) Oil or Fat

An oil or fat as an example of the lipophilic ingredient may be any of an oil or fat in a liquid state at room temperature, an oil or fat in a solid state at room temperature, and a mixture thereof. An oil or fat may include at least one selected from a monoglyceride, a diglyceride, and a triglyceride.

Examples of the oil or fat in a liquid state include olive oil, camellia oil, macadamia nut oil, castor oil, avocado oil, evening primrose oil, turtle oil, corn oil, mink oil, rapeseed oil, egg yolk oil, sesame oil, persic oil, wheat germ oil, sasanqua oil, linseed oil, safflower oil, cotton seed oil, perilla oil, soybean oil, peanut oil, tea seed oil, kaya oil, rice bran oil, china wood oil, tung oil, jojoba oil, germ oil, glycerin trioctanoate, glycerin triisopalmitate, salad oil, safflower oil (Carthamus tinctorius oil), palm oil, coconut oil, peanut oil, almond oil, hazelnut oil, walnut oil, and grape seed oil.

Examples of the oil or fat in a solid state include beef tallow, hydrogenated beef tallow, hoof oil, beef bone oil, mink oil, egg yolk oil, lard, horse fat, mutton tallow, hydrogenated oil, cacao butter, coconut oil, hydrogenated coconut oil, palm oil, palm hydrogenated oil, Japan tallow, Japan tallow kernel oil, and hydrogenated castor oil.

A medium-chain fatty acid triglyceride is also preferably used as the oil or fat. The term "medium-chain fatty acid glyceride" refers to a lipid composed of a saturated fatty acid of 6 to 12 carbon atoms, specifically, one of caproic acid, caprylic acid, capric acid, and lauric acid, esterified with glycerol. One to three fatty acids or any mixture thereof may be esterified with glycerol. In other words, the fat or oil may be any of a monoglyceride, a diglyceride, a triglyceride, and any mixture thereof. Unsaturated fatty acid-rich materials (e.g., olive oil and safflower oil) are liquid at room temperature, whereas saturated fatty acid-rich materials (e.g., coconut oil and palm oil) are solid at room temperature. Medium-chain fatty acid glycerides are contained in, for example, the palm oil and the coconut oil, and therefore are also preferably used. When a *Haematococcus alga* extract containing 18% by weight or more of astaxanthins is used, stable micelles can be formed by mixing the oil or fat with the *Haematococcus alga* extract.

In the present invention, the oil or fat may be a commercially available product. In the present invention, one oil or fat may be used alone, or two or more oils and/or fats may be used in combination.

(b) Phospholipid

In the emulsion composition of the present invention, the phospholipid is a complex lipid in the form of an ester, which includes fatty acid, alcohol, phosphoric acid, and nitrogen compound moieties. Phospholipids are a group of esters including phosphoric acid esters and fatty acid esters. Phospholipids can be broadly divided into glycerophospholipids having a glycerin backbone and sphingophospholipids having a sphingosine backbone. Hereinafter, they will be described in detail.

Examples of glycerophospholipids include phosphatidic acid, bisphosphatidic acid, lecithin (phosphatidylcholine), phosphatidylethanolamine, phosphatidylmethylethanolamine, phosphatidylserine, phosphatidylinositol, phosphatidylglycerin, diphosphatidylglycerin (cardiolipin), and various types of lecithin derived from plant sources such as soybeans, corn, peanuts, rapeseeds, and cereal plants such as wheat, animal sources such as egg yolk and cattle, and microorganism sources such as *Escherichia coli*. Sphingophospholipids include, for example, sphingomyelin.

In the present invention, enzymatically decomposed glycerophospholipids may be used. For example, lysolecithin obtained by enzymatic hydrolysis of the lecithin (enzymatically decomposed lecithin) lacks one of the fatty acid groups (acyl groups) bonded to the 1- or 2-position of glycerophospholipid. Reducing the number of fatty acid groups to one makes it possible for lecithin to have improved hydrophilicity and improved emulsifying or dispersing properties in water. Lysolecithin can be obtained not only by hydrolysis of lecithin in the presence of an acid or alkali catalyst but also by hydrolysis of lecithin with phospholipase A1 or A2. Examples of lyso compounds typified by lysolecithin include lisophosphatidic acid, lysophosphatidylglycerin, lysophosphatidylinositol, lysophosphatidylethanolamine, lysophosphatidylmethylethanolamine, lysophosphatidylcholine (lysolecithin), and lysophosphatidylserine.

Hydrogenated or hydroxylated glycerophospholipids, such as hydrogenated or hydroxylated lecithin may also be used in the present invention. The hydrogenation can be performed by, for example, allowing lecithin to react with hydrogen in the presence of a catalyst, in which the unsaturated bond in the fatty acid moiety is converted to a saturated bond by hydrogenation. The hydrogenation improves the oxidation stability of lecithin. The hydroxylation can be performed by heating lecithin in the presence of hydrogen peroxide at a high concentration and an organic acid such as acetic acid, tartaric acid, or butyric acid, in which the unsaturated bond in the fatty acid moiety is hydroxylated. The hydroxylation improves the hydrophilicity of lecithin.

Among the above, lecithin (a glycerophospholipid) or lysolecithin is preferred, and lecithin is more preferred.

In the present invention, the phospholipids may be used alone or in combination of two or more.

In general, lecithin is available in the form of a paste, a high-purity product, or an enzymatically decomposed product (lysolecithin). Paste type lecithin is more preferred. For example, a product with a phospholipid purity of 40% by weight or more is generally used. Alternatively, a product with a higher phospholipid purity may also be used. The purity is more preferably 50% by weight or more, even more preferably 60% by weight or more. Examples of the phospholipid that are preferably used include products available from Tsuji Oil Mills Co., Ltd., such as SLP-Paste (with a phospholipid content of 60% or more), SLP-Paste SP (with a phospholipid content of 60% or more), SLP-White (with a phospholipid content of 96% or more), SLP-Granular Lecithin (with a phospholipid content of 96% or more), SLP-Paste Lyso (with a lysophospholipid content of 40% or more), SLP-White Lyso (with a lysophospholipid content of 92% or more), SLP-PC35 (with a phospholipid content of 50% or more), SLP-PC70 (with a phospholipid content of 90% or more), and SLP-PI Powder A (with a phospholipid content of 95% or more).

(c) Polyol

In the emulsion composition of the present invention, the polyol has the functions of controlling viscosity and reducing the interfacial tension between water and the oil or fat ingredient so that expansion of the interface can be facilitated to make it easy to form a stable emulsion composition. The polyol may be any dihydric or polyhydric alcohol. Examples of the polyol include glycerin, diglycerin, triglycerin, polyglycerin, 3-methyl-1,3-butanediol, 1,3-butylene glycol, isoprene glycol, polyethylene glycol, 1,2-pentanediol, 1,2-hexanediol, propylene glycol, dipropylene glycol, polypropylene glycol, ethylene glycol, diethylene glycol, pentaerythritol, neopentyl glycol, maltitol, reduced starch syrup, fructose, glucose, sucrose, lactitol, palatinit, erythritol, sorbitol, mannitol, xylitol, xylose, glucose, lactose, mannose, maltose, galactose, fructose, inositol, pentaerythritol, maltotriose, sorbitol, sorbitan, trehalose, sugars obtained by degradation of starch, and sugar alcohols obtained by reducing the starch-degraded sugars.

In the present invention, these polyols may be used alone or in combination of two or more. The polyol is preferably at least one selected from glycerin, diglycerin, propylene glycol, ethylene glycol, 1,3-butylene glycol, polyethylene glycol, sorbitol, mannitol, dipropylene glycol, and sorbitan. The composition more preferably contains at least glycerin.

(d) Water

The emulsion composition of the present invention contains water. The water may be of any type used in food, pharmaceutical, and cosmetic products. For example, pure water, ion-exchanged water, alkaline ionized water, deep water, vibrated water, or natural water may be used.

(e) Sucrose Fatty Acid Ester

In the emulsion composition of the present invention, the sucrose fatty acid ester is an ester of sucrose and a fatty acid obtained from an oil or fat. Examples of the fatty acid include, but are not limited to, higher (C12 to C22) fatty acids such as lauric acid, myristic acid, palmitic acid, stearic acid, oleic acid, linoleic acid, and linolenic acid; and lower or medium (C2 to C11) fatty acids such as acetic acid, isobutyric acid, caprylic acid, and capric acid. The sucrose fatty acid ester is characterized in that it can have a wider balance between hydrophilicity and lipophilicity than other emulsifying agents and can have a higher HLB. The sucrose fatty acid ester can be used not only as an emulsifying agent but also as an agent for other purposes such as controlling viscosity, preventing retro-gradation of starch, and improving food feeling.

In the emulsion composition of the present invention, the sucrose fatty acid ester is preferably such that at least one hydroxyl group of sucrose forms an ester bond with a C8 to C22 fatty acid. More preferably, the sucrose fatty acid ester is such that at least one hydroxyl group of sucrose forms an ester bond with a C12 to C22 fatty acid. The sucrose fatty acid ester may be any of a monoester and a diester. One sucrose fatty acid ester may be used alone, or two or more sucrose fatty acid esters may be used in combination. Preferred examples of the sucrose fatty acid ester include sucrose monooleate, sucrose monostearate, sucrose monopalmitate, sucrose monomyristate, sucrose monolaurate, sucrose dioleate, sucrose distearate, sucrose dipalmitate, sucrose dimyristate, and sucrose dilaurate. Sucrose monostearate, sucrose monopalmitate, and sucrose monomyristate are more preferred.

(f) Polyglycerol Fatty Acid Ester

In the emulsion composition of the present invention, the polyglycerol fatty acid ester is an ester of a polyglycerol and a fatty acid. The polyglycerol fatty acid ester is preferably an ester of a polyglycerol with an average degree of polymerization of from 5 to 15 and C8 to C18 fatty acid. Preferred examples of the polyglycerol fatty acid ester include hexaglycerol monooleate, hexaglycerol monostearate, hexaglycerol monopalmitate, hexaglycerol monomyristate, hexaglycerol monolaurate, decaglycerol monooleate, decaglycerol monostearate, decaglycerol monopalmitate, decaglycerol monomyristate, decaglycerol monolaurate, glycerol stearate citrate, decaglycerol distearate, and decaglycerol monomyristate. Decaglycerol monolaurate, decaglycerol distearate, and decaglycerol monomyristate are more preferred.

[Optional Emulsifying Agent]

In addition to the sucrose fatty acid ester (e) and the polyglycerol fatty acid ester (f), the emulsion composition of the present invention may contain an optional emulsifying agent such as a saponin and/or a sorbitan fatty acid ester.

The saponin is obtained by extraction of *Sophora japonica* flower, *Quillaja saponaria* bark, soybeans, tea seeds, or other materials.

The sorbitan fatty acid ester preferably includes a fatty acid of 8 or more carbon atoms, more preferably a fatty acid of 12 or more carbon atoms. The sorbitan fatty acid ester may be any of a monoester and a diester. One sorbitan fatty acid ester may be used alone, or two or more sorbitan fatty acid esters may be used in combination. Preferred examples of the sorbitan fatty acid ester include sorbitan monooleate, sorbitan monostearate, sorbitan monopalmitate, sorbitan monomyristate, sorbitan monolaurate, sorbitan dioleate, sorbitan distearate, sorbitan dipalmitate, sorbitan dimyristate, and sorbitan dilaurate.

(g) Antioxidant

The emulsion composition of the present invention may optionally contain an antioxidant. Antioxidant compound groups (g-1) to (g-3) will be shown as specific examples. It will be understood that these compounds are not intended to limit the range of the antioxidant that may be used in the present invention.

(g-1) Ascorbic Acid, Erythorbic Acid, Derivatives Thereof, or Salts Thereof

Examples of ascorbic acid, ascorbic acid derivatives, or salts thereof include L-ascorbic acid, sodium L-ascorbate, potassium L-ascorbate, calcium L-ascorbate, L-ascorbyl phosphate, magnesium L-ascorbyl phosphate, L-ascorbyl sulfate, disodium L-ascorbyl sulfate, and L-ascorbyl-2-glucoside. Among them, L-ascorbic acid, sodium L-ascorbate, L-ascorbyl-2-glucoside, magnesium L-ascorbyl phosphate, and disodium L-ascorbyl sulfate are particularly preferred.

Examples of erythorbic acid, erythorbic acid derivatives, or salts thereof include erythorbic acid, sodium erythorbate, potassium erythorbate, calcium erythorbate, erythorbic acid phosphate, and erythorbic acid sulfate. Among them, erythorbic acid and sodium erythorbate are particularly preferred.

In general, commercially available products may be appropriately used as antioxidants belonging to the compound group (g-1). Examples include L-ascorbic acid (available from, for example, Takeda Pharmaceutical Company Ltd., Fuso Chemical Co., Ltd., BASF Japan Ltd., and Daiichi Seiyaku Co., Ltd.), sodium L-ascorbate (available from, for example, Takeda Pharmaceutical Company Ltd., Fuso Chemical Co., Ltd., BASF Japan Ltd., and Daiichi Seiyaku Co., Ltd.), ascorbyl-2-glucoside (AA-2G (trade name, Hayashibara Biochemical Laboratories Inc.), magnesium L-ascorbyl phosphate (e.g., Ascorbyl PM (trade name, Showa Denko K.K.), NIKKOL VC-PMG (trade name, Nikko Chemicals Co., Ltd.), and C Mate (trade name, Takeda Pharmaceutical Company Ltd.)).

(g-2) Polyphenols

The polyphenol compound group includes flavonoids (e.g., catechin, anthocyanin, flavone, isoflavone, flavane, flavanone, rutin, and glycosides thereof), phenolic acids (e.g., chlorogenic acid, ellagic acid, gallic acid, and propyl gallate), lignans, curcumins, and coumarins. Natural product-derived extracts as shown below contain relatively large amounts of these compounds. Therefore, these compounds may be used in the form of extracts.

Examples include licorice extracts, cucumber extracts, *Millettia reticulata* extracts, gentian (*Gentiana scabra*) extracts, *Geranium thunbergii* extracts, cholesterol and derivatives thereof, hawthorn extracts, Chinese peony extracts, ginkgo extracts, *Scutellaria baicalensis* (Scutellariae Radix) extracts, carrot extracts, *Rosa rugosa* (Japanese rose) extracts, *Cassia nomame* (*Cassia*) extracts, *Potentilla tormentilla* extracts, parsley extracts, *Paeonia suffruticosa* Andrews (Moutan Cortex) extracts, *Chaenomeles lagenariakoidz* (Japanese quince) extracts, *Melissa officinalis* extracts, yashajitu (yasha) extracts, *Saxifraga stolonifera* extracts, rosemary (*Rosmarinus officinalis*) extracts, lettuce extracts, tea extracts (e.g., oolong tea, red tea, and green tea), microorganism fermentation products, and Momordicae *Grosvenori* extracts (the term inside the parentheses is another name of the plant, the galenical name, or the like). Among these polyphenols, catechin, rosemary extracts, glucosyl rutin, ellagic acid, and gallic acid are particularly preferred.

In general, commercially available products may be appropriately used as antioxidants belonging to the compound group (g-2). Examples include ellagic acid (available from, for example, Wako Pure Chemical Industries, Ltd., etc.), rosemary extracts (e.g., RM-21A and RM-21E (trade names, Mitsubishi-Kagaku Foods Corporation)), catechin (e.g., Suncatol W-5 and Suncatol No. 1 (trade names, Taiyo Kagaku Co., Ltd.)), sodium gallate (e.g., Suncatol (trade name, Taiyo Kagaku Co., Ltd.)), and rutin/glucosylrutin/enzymatically decomposed rutin (e.g., Rutin K-2 and Rutin P-10 (trade names, Kiriya Chemical Co., Ltd.), and αG Rutin (trade name, Hayashibara Biochemical Laboratories Inc.).

(g-3) Radical Scavenger

A radical scavenger is an additive that inhibits the generation of radicals and traps the generated radicals as quickly as possible to play a role in blocking chain reaction (reference: "Yukagaku Binran (A Handbook of Oil Chemistry), 4th ed.," edited by Japan Oil Chemists' Society, 2001). Known methods for directly checking whether a material functions as a radical scavenger include mixing the material with a reagent and measuring how the material traps radicals by means of a spectrophotometer or an ESR (electron spin resonance) spectrometer. In such methods, DPPH (1,1-diphenyl-2-picrylhydrazyl) or galvinoxyl radical is used as the reagent. In the present invention, the radical scavenger is defined as a compound with which the time required to increase the peroxide value (POV) of an oil or fat to 60 meq/kg through auto-oxidation of the oil or fat under the experimental conditions below is twice or more, more preferably five times or more, that required for a blank.

Oil or fat: Olive oil

Amount of sample added: 0.1% by weight to the oil or fat

Test conditions: The sample is heated at 190° C. while the POV is measured over time, and the time required for the POV to reach 60 meq/kg is calculated.

A variety of antioxidants are shown in "Kosankazai no Riron to Jissai (Theory and Practice of Antioxidants)" written by Kajimoto and published by San Shobo (1984) and "Sanka Boshizai Handobukku (Handbook of Antioxidants)" written by Sawatari, Nishino, and Tabata and published by Taiseisha (1976). Among such antioxidants, any compound capable of functioning as a radical scavenger may be used as the radical scavenger for the present invention. Specific examples include compounds having a phenolic hydroxyl group, amine compounds such as phenylenediamine, and oil-solubilized derivatives of ascorbic acid and erythorbic acid.

Examples of the compounds having a phenolic hydroxyl group include guaiac resin, nordihydroguaiaretic acid (NDGA), gallic acid esters, BHT (butylhydroxytoluene), BHA (butylhydroxyanisol), tocopherols, and bisphenols. Examples of gallic acid esters include propyl gallate, butyl gallate, and octyl gallate.

Examples of the amine compounds include phenylenediamines. Diphenyl-p-phenylenediamine or 4-amino-p-diphenylamine is more preferred.

Examples of the oil-solubilized derivatives of ascorbic acid and erythorbic acid include L-ascorbyl stearate, L-ascorbyl tetraisopalmitate, L-ascorbyl palmitate, erythorbyl palmitate, and erythorbyl tetraisopalmitate.

[Content of Each Ingredient]

The content of the (a) lipophilic ingredient is preferably, but not limited to, 0.7 part by weight or more, more preferably from 0.8 to 40 parts by weight, even more preferably from 1.0 to 30 parts by weight, to 100 parts by weight of the total of the emulsion composition of the present invention, in view of allowing a carotenoid or the like to function in the emulsion composition and in view of stability and other properties.

The content of the (a-1) carotenoid is preferably, but not limited to, 0.7 part by weight or more, more preferably from 0.8 to 8.0 parts by weight, even more preferably from 1.0 to 6.0 parts by weight, to 100 parts by weight of the total of the emulsion composition of the present invention, in view of allowing the carotenoid to function and in view of stability and absorbability. When astaxanthin or a fatty acid ester thereof is added as the (a-1) carotenoid, the content of astaxanthin or the fatty acid ester thereof is preferably 0.7 part by weight or more, more preferably from 0.8 to 8.0 parts by weight, even more preferably from 1.0 to 6.0 parts by weight, to 100 parts by weight of the total of the emulsion composition of the present invention.

The content of astaxanthins (the total content of the free form of astaxanthin and an astaxanthin ester or esters) in all (a-1) carotenoids is preferably, but not limited to, from 60 to 100 parts by weight, more preferably from 70 to 95 parts by weight, even more preferably from 80 to 93 parts by weight, to 100 parts by weight of the carotenoids.

In view of the stability and absorbability of the carotenoid, the weight ratio of the (a-2) oil or fat to the (a-1) carotenoid is preferably, but not limited to, from 0.8 to 6.0 parts by weight, more preferably from 1.0 to 5.0 parts by weight, even more preferably from 1.2 to 3.0 parts by weight of acylglycerols (the total of triglyceride, diglyceride, and monoglyceride) to 1 part by weight of the carotenoid (a-1).

In view of the stability and absorbability of the astaxanthins, the weight ratio of the (a-2) oil or fat to the astaxanthins is preferably, but not limited to, from 2 to 14 parts by weight, more preferably from 2.5 to 10 parts by weight, even more preferably from 3 to 8 parts by weight of acylglycerols (the total of triglyceride, diglyceride, and monoglyceride) to 1 part by weight of the astaxanthins. When a *Haematococcus alga* extract is used for the astaxanthins, the weight ratio of acylglycerols to astaxanthin in the *Haematococcus alga* extract is preferably from 2 to 8 parts by weight of acylglycerols to 1 part by weight of the astaxanthins. Olive oil, camellia oil, and medium-chain fatty acid triglyceride may be added in an amount of from 0.2 to 1.5 parts by weight to 1 part by weight of the *Haematococcus alga* extract.

The content of the (b) phospholipid is preferably, but not limited to, from 2.0 to 15.0 parts by weight, more preferably from 2.5 to 10.0 parts by weight, even more preferably from 2.5 to 5.5 parts by weight, to 100 parts by weight of the total of the emulsion composition of the present invention. When the phospholipid content is 2.0 parts by weight or more, the emulsion composition will tend to have high stability. When the content is 15.0 parts by weight or less, an excess of phospholipid is prevented from separating from the lipophilic ingredient to form a phospholipid dispersion in water, so that the emulsion composition can be kept stable.

The weight ratio of the (b) phospholipid to the (a-1) carotenoid is preferably, but not limited to, from 1.1 to 4.5, more preferably from 1.3 to 2.5, even more preferably from 1.8 to 2.2, to 1 part by weight of the carotenoid.

The weight ratio of the (b) phospholipid to the astaxanthins is preferably, but not limited to, from 0.6 to 4.0 parts by weight, more preferably from 0.7 to 3.0 parts by weight, even more preferably from 0.8 to 2.5, to 1 part by weight of the astaxanthins.

The content of the (c) polyol is preferably, but not limited to, from 10 to 70 parts by weight, more preferably from 20 to 68 parts by weight, most preferably from 30 to 65 parts by weight, to 100 parts by weight of the total of the emulsion composition of the present invention. Preferably, when the polyol content is 10 parts by weight or more, sufficient storage stability can be easily achieved regardless of the type or content of the lipophilic ingredient, and setting the content at 70 parts by weight or less can exert a maximum effect.

The content of (d) water is preferably, but not limited to, from 5 to 70 parts by weight, more preferably from 7 to 50 parts by weight, even more preferably from 10 to 30 parts by weight, to 100 parts by weight of the total of the emulsion composition of the present invention. If the water content is more than 70 parts by weight, the content of the lipophilic ingredient will be relatively low, which is not preferred. If the water content is less than 5 parts by weight, the emulsion composition will have reduced stability and also have reduced dispersibility in an aqueous medium and be less soluble in water, so that the in vivo absorbability may also decrease. In one embodiment, the emulsion composition of the present invention may be encapsulated in hard or soft capsules. In this case, the water content is preferably 15 parts by weight or less to 100 parts by weight of the emulsion composition.

In view of the stability and absorbability of the (a-1) carotenoid, the weight ratio of (d) water to the (a-1) carotenoid is preferably, but not limited to, from 5 to 20 parts by weight, more preferably from 7 to 15 parts by weight of water to 1 part by weight of the carotenoid.

In view of the stability and absorbability of the astaxanthins, the weight ratio of (d) water to the astaxanthins is preferably, but not limited to, from 5 to 15 parts by weight, more preferably from 8 to 12 parts by weight of water to 1 part by weight of the astaxanthins.

The content of the (e) sucrose fatty acid ester is preferably, but not limited to, from 3 to 15 parts by weight, more preferably from 4 to 10 parts by weight, even more preferably from 5 to 8 parts by weight, to 100 parts by weight of the total of the emulsion composition of the present invention.

In view of the stability and absorbability of the (a) lipophilic ingredient, the ratio of the (e) sucrose fatty acid ester to the (a) lipophilic ingredient is preferably, but not limited to, from 30 to 70 parts by weight, more preferably from 40 to 50 parts by weight of the sucrose fatty acid ester, to 100 parts by weight of the lipophilic ingredient.

The content of the (f) polyglycerol fatty acid ester is preferably, but not limited to, from 1 to 10 parts by weight, more preferably from 1.5 to 8 parts by weight, even more preferably from 2 to 7 parts by weight, to 100 parts by weight of the total of the emulsion composition of the present invention.

The weight ratio of the (f) polyglycerol fatty acid ester to the (a) lipophilic ingredient is preferably, but not limited to, from 10 to 40 parts by weight, more preferably from 15 to 30 parts by weight of the polyglycerol fatty acid ester, to 100 parts by weight of the lipophilic ingredient.

In a preferred mode, the content of the (e) sucrose fatty acid ester is higher than that of the (f) polyglycerol fatty acid ester in view of the stability and absorbability of the (a) lipophilic ingredient. For example, the weight ratio of the (f) polyglycerol fatty acid ester to the (e) sucrose fatty acid ester is preferably from 0.1 to 0.9 part by weight, more preferably from 0.2 to 0.8 part by weight of the polyglycerol fatty acid ester to 1 part by weight of the sucrose fatty acid ester. The sucrose fatty acid ester has a sweet taste due to its sucrose structure. In contrast, the polyglycerol fatty acid ester and the phospholipid have a characteristic bitter taste and therefore should preferably be added in an amount smaller than that of the sucrose fatty acid ester. In general, the sucrose fatty acid ester tends to provide a higher HLB value (water solubility) than the polyglycerol fatty acid ester, which suggests that a higher content of the sucrose fatty acid ester may provide better compatibility with water.

The emulsion composition of the present invention may be of an oil-in-water (o/w) type or a water-in-oil (w/o) type. The composition of the present invention is preferably an oil-in-water emulsion in view of improved dispersibility in an aqueous medium and the high solubility in water. In a preferred mode of the present invention, the water content is from about 12 to about 15 parts by weight to 100 parts by weight of the total of the emulsion composition. Despite such a level of water content, an oil-in-water emulsion can be formed. This ability would make it possible to increase the content of the lipophilic ingredient, for example, to increase the content of a carotenoid as an active ingredient to 1.5 parts by weight or more to 100 parts by weight of the total of the emulsion composition, and would also contribute to an increase in the in vivo absorbability of the active ingredient while maintaining the dispersibility or solubility in water.

[Stability]

As used herein, the term "stability" refers to the stability of the emulsified state of the emulsion composition itself (emulsion stability) and the stability of the lipophilic ingredient (e.g., carotenoids, preferably astaxanthins) in the composition. More specifically, the emulsion stability means that in the emulsion composition, particles do not collapse or separate into oil layers and are uniform overall. The stability of the lipophilic ingredient particularly refers to the stability of carotenoids, preferably the stability of astaxanthins or other lipophilic materials sensitive to oxidative decomposition. In other words, the stability of the lipophilic ingredient indicates low rate of decrease in the amount of astaxanthins.

[Particle Size and Measurement Method]

In the emulsion composition of the present invention, the emulsion particles may have an average particle size of 150 nm or less, preferably 140 nm or less, more preferably 130 nm or less. The average particle size is preferably 70 nm or more, more preferably 95 nm or more, even more preferably 100 nm or more.

The particle size of the emulsion composition of the present invention can be measured with a commercially available particle size analyzer or the like. Known methods for measuring the particle size distribution of emulsion compositions include optical microscopy, confocal laser microscopy, electron microscopy, atomic force microscopy, static light scattering, laser diffraction, dynamic light scattering, centrifugal sedimentation, electrical pulse measurement, chromatography, and ultrasonic attenuation. Apparatuses corresponding to each principle are commercially available.

In the present invention, dynamic light scattering is preferably used to measure the particle size of the emulsion composition of the present invention in view of the particle size range and ease of the measurement. Examples of commercially available measurement apparatuses employing dynamic light scattering include NANOTRAC UPA (Nikkiso Co., Ltd.), a dynamic light scattering particle size analyzer LB-550 (HORIBA, Ltd.), and a concentrated system particle size analyzer FPAR-1000 (Otsuka Electronics Co., Ltd.), and Zetasizer Nano ZS (Malvern Instruments Ltd.).

In the present invention, the particle size is the value measured with a dynamic light scattering particle size analyzer Zetasizer Nano ZS (Malvern Instruments Ltd.). Specifically, the value measured as described below is used.

In the method for measuring the particle size, the sample is diluted with pure water and then subjected to the measurement using a quartz or polystyrol cell. The particle size can be determined as the median diameter with the refractive indexes of the sample and the dispersion medium set at 1.600 and 1.333 (pure water), respectively, and with the viscosity of the dispersion medium set as the viscosity of pure water.

The particle size of the emulsion composition can be micronized by means of not only the above ingredients of the emulsion composition but also other factors such as stirring conditions (e.g., shearing force, temperature, and pressure) and the ratio of oil phase and aqueous phase in the method described below for preparing the emulsion composition.

[Preparation Method]

Hereinafter, the method of preparing the emulsion composition of the present invention will be described. Any method generally used to prepare an aqueous solution containing a lipophilic ingredient may be used to form the emulsion composition of the present invention. In the preparation of the emulsion composition of the present invention, oil droplets with high emulsion stability can be easily formed without any especially strong stirring.

Specifically, the emulsion composition of the present invention can be prepared by a process that includes (1) mixing and dissolving a sucrose fatty acid ester and optionally a polyol in water to form an aqueous phase, (2) mixing and dissolving a lipophilic ingredient, oil-soluble surfactants such as a polyglycerol fatty acid ester and lecithin, and optionally a polyol to form an oil phase, and (3) mixing the aqueous phase and the oil phase.

The temperature of each phase and the mixing temperature may be appropriately selected in an arbitrary range from room temperature to 80° C. depending on the thermal stability, viscosity, solubility, and miscibility of the lipophilic ingredient. The mixing process and the dispersion process may be performed using a conventional emulsifying apparatus such as a conventional mixer, homomixer, continuous-flow shear mixer, high-pressure homogenizer, or ultrasonic disperser. In particular, the emulsion particle size of the lipophilic ingredient should be 300 nm or less, specifically, 150 nm or less. If higher transparency or permeability needs to be imparted, a strong mixer such as a high-pressure homogenizer should be used.

When the emulsion composition is colored with a colorant, the composition may be subjected to defoaming by a conventional method, for example, using HIVIS DAPPER (trade name, manufactured by PRIMIX Corporation).

The emulsion composition of the present invention is soluble in water and can be easily mixed into aqueous beverages, aqueous food products, pharmaceuticals, cosmetics, and other products.

When the emulsion composition of the present invention is added to a beverage, a food product, a cosmetic, a pharmaceutical, or the like, the content of the composition may be, for example, in the range of from 0.0001 to 40% by weight, preferably in the range of from 0.001 to 10% by weight to the total weight of the product, although it depends on the type or purpose of the product.

When the carotenoid is added as a colorant, the content of the carotenoid may be controlled as appropriate depending on the color tone of the product. When the carotenoid is mixed as an active ingredient, it should be added in a sufficiently effective amount.

Examples of food products include, but are not limited to, margarine, butter, butter sauce, cheese, fresh cream, shortening, lard, ice cream, yogurt, dairy products, meat sauce products, fish products, pickles, fried potato, potato chips, snack foods, thin slices of dried rice cake, popcorn, seasoned powder for sprinkling over rice, chewing gum, chocolate, pudding, jelly, gummi-candy, candy, drops, caramel, bread, sponge cake, cake, doughnut, biscuit, cookie, cracker, macaroni, pasta, Chinese noodles, buckwheat noodles, wheat-flour noodles, salad oils, instant soup, dressing, egg, mayonnaise, miso, and other food products or food raw materials.

Examples of beverages include, but are not limited to, vegetable drinks, fruit drinks, refreshing drinks, sport drinks, tea beverages, coffee beverages, cocoa beverages, carbonated drinks, non-alcoholic beverages, alcoholic beverages, or any combinations thereof. In particular, the emulsion composition of the present invention can be successfully added to alcoholic beverages or acidic beverages, for which emulsion stability has been conventionally considered to be difficult to maintain.

Examples of cosmetics and skin pharmaceuticals for external use include, but are not limited to, emulsions, creams, skin lotions, packs, dispersions, cleansing agents, makeup cosmetics, scalp or hair care products, and other cosmetics, and ointments, creams, liquids for external use, and other pharmaceuticals. Besides the ingredients described above, if necessary, the emulsion composition may appropriately contain an ingredient commonly used in cosmetics, pharmaceuticals, or external preparations for skin, such as a whitening agent, a moisturizing agent, any skin nutrient, an ultraviolet absorber, an antioxidant, a lipophilic material, a surfactant, a thickener, an alcohol, a colorant, water, an antiseptic, or a perfume.

The emulsion composition of the present invention may be used to form internal solid preparations or internal liquid preparations for oral administration or to form injections, external preparations, suppositories, inhalants, or transnasal preparations for parenteral administration.

Internal medicines for oral administration include, for example, capsules. Capsules include hard and soft capsules. Base materials that may be used for capsules include, but are not limited to, gelatin derived from bovine bones, bovine skins, pig skins, or fish skins; materials usable as food additives, such as seaweed-derived products such as carrageenan and alginic acid, vegetable seed-derived products such as locust bean gum and guar gum, microorganism-derived products such as pullulan and curdlan; manufacturing agents such as celluloses; and other base materials.

Such internal solid preparations can be formulated by conventional methods using the emulsion composition of the present invention as it is or using a mixture of the emulsion composition of the present invention and an additional material such as a vehicle (e.g., lactose, mannitol, glucose, microcrystalline cellulose, or starch), a binder (e.g., hydroxypropyl cellulose, polyvinylpyrrolidone, or magnesium aluminometasilicate), a disintegrator (e.g., calcium carboxymethyl cellulose), a lubricant (e.g., magnesium stearate), a stabilizer, or a solubilizing aid (e.g., glutamic acid or aspartic acid). If necessary, capsules may be coated with a coating agent (e.g., sucrose, gelatin, hydroxypropyl cellulose, or hydroxypropyl methylcellulose phthalate) or coated with two or more layers. Capsules of an absorbable material such as gelatin may also be encompassed.

Internal liquid preparations for oral administration include pharmaceutically acceptable solutions, suspensions, emulsions, syrups, and elixirs. To form such liquid preparations, one or more active materials are dissolved, suspended, or emulsified in a common diluent (e.g., purified water, ethanol, or a mixture thereof). Such liquid preparations may contain a moistening agent, a suspending agent, an emulsifying agent, a sweetener, a flavor, an aromatic, a preservative, or a buffer.

Dosage forms of external preparations for parenteral administration includes, for example, ointments, gels, creams, fomentations, patches, liniments, nebulas, inhalants, sprays, aerosols, eye drops, and nasal drops.

[In Vivo Absorbability]

The emulsion composition of the present invention provides high in vivo absorbability for the lipophilic ingredient. As used herein, the term "in vivo absorbability" refers to the level of the ability of an active ingredient, such as a carotenoid as an example of the lipophilic ingredient (a), to be absorbed from the digestive tract into the blood when the emulsion composition of the present invention, a beverage or food product containing it, or a pharmaceutical or any other product containing it is taken or administered orally. Specifically, the emulsion composition of the present invention has 1.2 to 10 times, preferably 1.5 to 5 times as high absorbability as commonly distributed *Haematococcus alga* extracts among commercially available astaxanthins, for mammals. When the emulsion composition of the present invention is added to transdermal preparations such as cosmetics, the term "in vivo absorbability" refers to the level of the ability of an active ingredient to be transdermally absorbed and utilized at the desired topical cite. The in vivo absorbability of the emulsion composition of the present invention can be measured by an in vitro method using an isolated intestinal tract or by an in vivo method using experimental animals, which will be easily understood by those skilled in the art with reference to the examples below.

EXAMPLES

Hereinafter, the present invention will be more specifically described with reference to examples, which, however, are not intended to limit the present invention.

[Particle Size Measurement]
Equipment and Materials
  Analyzer: Zetasizer Nano ZS (Malvern Instruments Ltd.)
  Cell: Dispo Cell (Dispo Cell #1960 manufactured by Kartell) Analyzer settings
  Preset in-cell temperature 40° C.
  Sample refractive index 1.60, dispersion medium refractive index 1.330, the value of pure water viscosity is used as the value of dispersion medium viscosity.
Measurement Procedure
  The emulsion composition and ion-exchanged water were heated to 40 to 45° C. and then subjected to the measurement. To 20 g of ion-exchanged water was added 0.04 g of the emulsion composition and stirred until uniform. The mixture was further so diluted with ion-exchanged water that the attenuator of the analyzer indicated 7 to 10, and the dilution was measured.

Example 1

Glycerin (58 g) was heated to 50° C., to which a polyglycerol fatty acid ester (3 g), AstaReal Oil 200SS (7.5 g), mixed tocopherols (0.5 g), and lecithin (6 g) were added. The materials were mixed and dissolved to form an oil phase. At 50° C., a sucrose fatty acid ester (6 g) was added to water (14 g) to form an aqueous phase. The oil phase and the aqueous phase were mixed and emulsified. The emulsion was then subjected to high-pressure emulsification with a high-pressure homogenizer, resulting in an astaxanthins-containing emulsion composition.

AstaReal 200SS (manufactured by Fuji Chemical Industries Co., Ltd.) is a lipophilic extract obtained from *Haematococcus alga*, which contains about 20% of astaxanthin as calculated in terms of the free form. The polyglycerol fatty acid ester was Decaglyn 1-L (HLB 15.5) manufactured by Nikko Chemicals Co., Ltd. The lecithin was SLP-Paste (SP Lecithin Paste) (lecithin content 60% or more) manufactured by Tsuji Oil Mills Co., Ltd. The sucrose fatty acid ester was DK ESTER SS (HLB 19) manufactured by DKS Co., Ltd. Palm oil was used as a medium-chain fatty acid triglyceride. The high-pressure homogenizer used was Star Burst HJP-25001 manufactured by Sugino Machine Limited.

Example 2

Using the same process as in Example 1, an emulsion composition was prepared according to the formulation shown in Table 1.

TABLE 1

| Raw materials | Example 1 | Example 2 |
| --- | --- | --- |
| AstaReal 200SS Oil (astaxanthins content 20.3%, non-astaxanthins carotenoid content 3.2%, acylglycerol content 59.5%) | 7.5 | 5.0 |

TABLE 1-continued

| Raw materials | Example 1 | Example 2 |
| --- | --- | --- |
| Lecithin paste (lecithin content 60% or more) | 6.0 | 6.0 |
| Medium-chain fatty acid triglyceride | 5.0 | 5.0 |
| Mixed tocopherols | 0.5 | 0.5 |
| Sucrose fatty acid ester (DK ESTER SS (DKS Co., Ltd.)) | 6.0 | 6.0 |
| Decaglycerol monolaurate (Decaglyn 1-L (Nikko Chemicals Co., Ltd.)) | 3.0 | 3.0 |
| Glycerin | 58.0 | 60.5 |
| Water | 14.0 | 14.0 |
| Total (g) | 100.0 | 100.0 |

Example 3

Using the same process as in Example 1, emulsion compositions were prepared according to the formulations shown in Table 2.

TABLE 2

| | Example No. | | | |
| --- | --- | --- | --- | --- |
| Raw materials | 3-1 Weight | 3-2 Weight | 3-3 Weight | 3-4 Weight |
| AstaReal 200SS Oil (astaxanthins content 20.3%, non-astaxanthins carotenoid content 3.2%, acylglycerol content 59.5%) | 7.5 | 7.5 | 7.5 | 7.5 |
| Lecithin paste (lecithin content 60% or more) | 4.0 | 7.0 | 8.0 | 10.0 |
| Medium-chain fatty acid triglyceride | 5.0 | 5.0 | 5.0 | 5.0 |
| Mixed tocopherols | 0.5 | 0.5 | 0.5 | 0.5 |
| Sucrose fatty acid ester (DK ESTER SS (DKS Co., Ltd.)) | 6.0 | 6.0 | 6.0 | 6.0 |
| Decaglycerol monolaurate (Decaglyn 1-L (Nikko Chemicals Co., Ltd.)) | 3.0 | 3.0 | 3.0 | 3.0 |
| Glycerin | 57.0 | 56.0 | 56.0 | 56.0 |
| Water | 14.0 | 14.0 | 14.0 | 14.0 |
| Total (g) | 100.0 | 100.0 | 100.0 | 100.0 |

Example 4

Using the same process as in Example 1, emulsion compositions were prepared according to the formulations shown in Table 3.

TABLE 3

| | Example No. | | |
| --- | --- | --- | --- |
| Raw materials | 4-1 Weight | 4-2 Weight | 4-3 Weight |
| AstaReal 200SS Oil (astaxanthins content 20.3%, non-astaxanthins carotenoid content 3.2%, acylglycerol content 59.5%) | 10.0 | 12.5 | 15.0 |
| Lecithin paste (lecithin content 60% or more) | 6.0 | 6.0 | 6.0 |
| Medium-chain fatty acid triglyceride | 5.0 | 5.0 | 5.0 |
| Mixed tocopherols | 0.5 | 0.5 | 0.5 |
| Sucrose fatty acid ester (DK ESTER SS (DKS Co., Ltd.)) | 6.0 | 6.0 | 6.0 |
| Decaglycerol monolaurate (Decaglyn 1-L (Nikko Chemicals Co., Ltd.)) | 3.0 | 3.0 | 3.0 |

TABLE 3-continued

|  | Example No. | | |
| --- | --- | --- | --- |
| Raw materials | 4-1 Weight | 4-2 Weight | 4-3 Weight |
| Glycerin | 55.5 | 53.0 | 50.5 |
| Water | 14.0 | 14.0 | 14.0 |
| Total (g) | 100.0 | 100.0 | 100.0 |

Comparative Example 1

Compositions were prepared according to the formulations shown in Table 4, which include a formulation (Comparative Example 1-1, Reference Example) corresponding to the composition of Example 1 shown in Patent Literature 1 (JP 2011-92083 A) and formulations with higher astaxanthins contents (Comparative Examples 1-2 and 1-3).

TABLE 4

|  | Comparative Example No. | | |
| --- | --- | --- | --- |
| Raw materials | 1-1 Weight | 1-2 Weight | 1-3 Weight |
| Sucrose fatty acid ester | 4.0 | 4.0 | 4.0 |
| Polyglycerol fatty acid ester | 3.0 | 3.0 | 3.0 |
| Glycerin | 50.0 | 40.0 | 30.0 |
| AstaReal 50F Oil (astaxanthins content 5.4%, non-astaxanthins carotenoid content 0.6%, acylglycerol content 80.2%) | 10.0 | 20.0 | 30.0 |
| Mixed tocopherols | 0.5 | 0.5 | 0.5 |
| Lecithin paste (lecithin content 60% or more) | 2.0 | 2.0 | 2.0 |
| Water | 30.5 | 30.5 | 30.5 |
| Total (g) | 100.0 | 100.0 | 100.0 |

Comparative Example 2

A composition was prepared according to the formulation shown in Table 5, which was with reference to the composition of Example E-01 shown in Patent Literature 2 (JP 2008-13751 A). The lecithin used was Lecion P (lecithin content 90% or more) manufactured by Riken Vitamin Co., Ltd.

TABLE 5

| Raw materials | Comparative Example No. 2 Weight |
| --- | --- |
| Sucrose stearate | 1.3 |
| Decaglyceryl monooleate | 2.5 |
| Glycerin | 50.0 |
| AstaReal 200SS Oil (astaxanthins content 20.3%, non-astaxanthins carotenoid content 3.2%, acylglycerol content 59.5%) | 4.0 |
| Mixed tocopherols | 1.0 |
| Lecithin (Lecion P manufactured by Riken Vitamin Co., Ltd.) | 9.0 |
| Water | 32.2 |
| Total (g) | 100.0 |

Comparative Example 3

A composition was prepared according to the formulation shown in Table 6, which was with reference to the composition of Example EM-01 shown in Patent Literature 3 (JP 2008-154577 A).

TABLE 6

| Raw materials | Comparative Example No. 3 Weight |
| --- | --- |
| Sucrose stearate | 3.3 |
| Decaglyceryl monooleate | 6.7 |
| Glycerin | 45.0 |
| AstaReal 200SS Oil (astaxanthins content, 20% acylglycerol content 60%) | 3.75 |
| Mixed tocopherols | 0.95 |
| Coconut oil | 9.3 |
| Lecithin (Lecion P manufactured by Riken Vitamin Co., Ltd.) | 1.0 |
| Water | 30.0 |
| Total (g) | 100.0 |

[Stability Test]

The emulsion composition (1 g) was placed and sealed in a 10 mL vessel. The vessel was then stored in a thermostat kept at 50° C. After four (or two) weeks, the residual amount of astaxanthins in the composition (50° C.-4w or 50° C.-2w) was measured, and the appearance of the composition was visually observed.

[Residual Amount of Astaxanthins]

The absorbance of the emulsion composition was measured using Ubest-50 Spectrophotometer manufactured by JASCO Corporation. 50 mg of the resulting emulsion was diluted with acetone to 100 mL. The absorbance of the emulsion was measured at a wavelength of 474 nm, using acetone as a reference. The residual amount of astaxanthins was determined as the ratio to the residual amount at the time of preparation.

[Results]

The results are shown in Table 7 below.

TABLE 7

|  | Residual amount of astaxanthins (Stability of astaxanthins) | Appearance immediately and 4 weeks after preparation | Average particle size (nm) |
| --- | --- | --- | --- |
| Example 1 | 50° C.-4 w: 98.3% | No separation at both stages | 111 |
| Example 3-1 | 50° C.-4 w: 94.4% | No separation at both stages | 109.1 |
| Example 3-2 | 50° C.-4 w: 90.3% | No separation at both stages | 101.8 |
| Example 3-3 | 50° C.-4 w: 90.2% | No separation at both stages | 108.3 |
| Example 3-4 | 50° C.-4 w: 95.9% | No separation at both stages | 111.3 |
| Example 4-1 | 50° C.-4 w: 94.1% | No separation at both stages | 104.7 |
| Example 4-2 | 50° C.-4 w: 97.2% | No separation at both stages | 118.4 |
| Example 4-3 | 50° C.-4 w: 94.4% | No separation at both stages | 114.5 |
| Comparative Example 1-1 | 50° C.-4 w: 94.6% | No separation at both stages | 126.4 |
| Comparative Example 1-2 | No data, because emulsion was not obtainable | Not uniformly prepared and not emulsified | — |

TABLE 7-continued

|  | Residual amount of astaxanthins (Stability of astaxanthins) | Appearance immediately and 4 weeks after preparation | Average particle size (nm) |
|---|---|---|---|
| Comparative Example 1-3 | No data, because emulsion was not obtainable | Not uniformly prepared and not emulsified | — |
| Comparative Example 2 | No data, because emulsion was not obtainable | Solidified during preparation and not dispersed | — |
| Comparative Example 3 | No data, because emulsion was not obtainable | Solidified during preparation and not dispersed | — |

Results and Discussion

Even after standing for 2 to 4 weeks, astaxanthins remained at a high concentration in the emulsion compositions according to the present invention. In the composition of Comparative Example 1-1, no separation was observed at the time of preparation and after 4 weeks. The compositions of Comparative Examples 1-2 and 1-3 were insufficiently emulsified and not made uniform. The compositions of Comparative Examples 1-1, 1-2, and 1-3 were prepared with different concentrations of astaxanthin from the same astaxanthin oil. In Comparative Example 1-1, the concentration of astaxanthins was about 0.5%. In Comparative Examples 1-2 and 1-3, the concentration was increased to 1.0% and 1.5%, respectively, so that no uniform emulsion compositions were able to be prepared.

In Comparative Examples 2 and 3, aggregation occurred in the mixture being prepared, so that no emulsion was formed. In Comparative Example 2, the mixture solidified during the preparation of the oil phase, which was insufficiently scraped when mixed with the aqueous phase. Coarse solids occurred in the mixture being emulsified and made it impossible to uniformly mix the materials. Also in Comparative Example 3, a small amount of small solids occurred in the mixture when the oil phase and the aqueous phase were mixed and emulsified, so that they were not able to be mixed uniformly.

In Comparative Examples 1-2, 1-3, 2, and 3, the compositions were no longer subjected to the examination of absorbability and the measurement of particle size.

[Absorbability Test]

Bioavailability was determined when the composition was administered to rats and humans.

<Astaxanthins Absorbability Test on Rats>
Feeding Method

Wistar rats (male, four or five rats per group, 250 to 300 g weight, 6 to 8 week old) were fasted overnight. Using a feeding needle, the composition was then administered in such a way that astaxanthins were administered in an amount of 100 mg/kg rat weight. Subsequently, 3, 6, 9, and 12 hours after the administration, blood was collected from the jugular vein of the rats, and the plasma was separated from the blood (no data for the blood collection after 12 hours with respect to Comparative Example 1-1).

[Measurement of Amount of Astaxanthins in Blood]

A 0.1 mL aliquot was taken from the obtained plasma. Subsequently, 5 mL of hexane was added to the aliquot and then vigorously mixed so that astaxanthins were extracted from the plasma. The extract was then centrifuged, and the resulting hexane layer was collected in another test tube. 5 mL of the resulting hexane extract was evaporated under reduced pressure to dryness. The residue was then mixed with 0.1 mL of acetone and dissolved. Under the conditions below, 0.05 mL of the resulting acetone solution was analyzed by HPLC, and the concentration of astaxanthins in the plasma was determined.

HPLC analysis conditions: column, YMC & nbsp Carptenoid Column; mobile phase, methanol:tert-butyl methyl ether:1% phosphoric acid=81:15:4 (V:V:V); linear gradient elution; detection wavelength, 470 nm; flow rate, 1.0 mL/min; column temperature, 25° C.

FIG. 1 shows the results (average values) of the absorbability test on rats for the compositions of Examples 1 and 2, the composition of Comparative Example 1-1, and a commercially available 10% astaxanthins-containing oil (AstaReal L10 manufactured by Fuji Health Sciences, Inc.). Table 8 shows the AUC (area under the curve) from 0 to 9 hours for each sample.

TABLE 8

|  | Example 1 | Example 2 | L10 oil | Comparative Example 1-1 |
|---|---|---|---|---|
| $AUC_{0-9\ hr}$ (ng/mL)·hr | 597.8 ± 266.0 | 606.3 ± 181.4 | 131.0 ± 77.3 | 232.4 ± 72.8 |

<Astaxanthins Absorbability Test on Humans>
Intake Procedure

Four male and female adults each took two soft capsules filled with the composition (containing 3 mg of astaxanthins). Subsequently, 3, 6, and 9 hours after the administration, blood was collected from the arm vein, and the plasma was separated from the blood. The measurement of astaxanthins in the blood was performed by the same method as in the astaxanthins absorbability test on rats.

Figure 2:
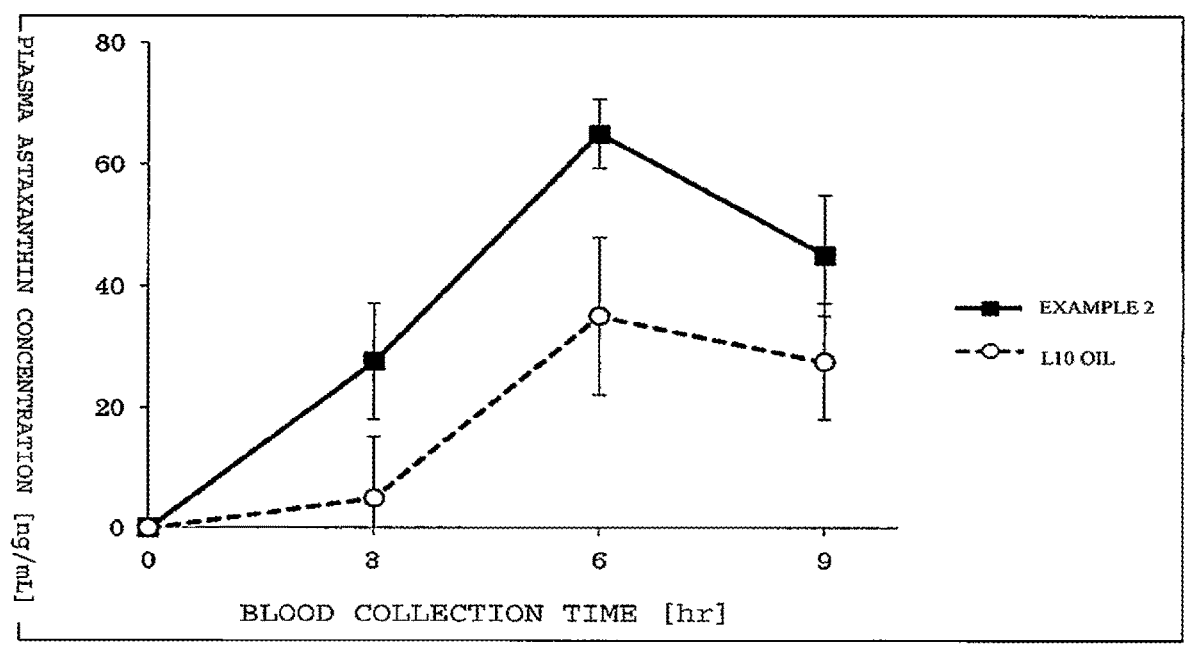
FIG. 2 illustrates the results of an absorbability test on humans who take the emulsion composition of the present invention.

FIG. 2 shows the results (average values) of the absorbability test on rats for the composition of Example 2 and a commercially available 10% astaxanthins-containing oil (AstaReal L10 manufactured by Fuji Health Sciences, Inc.). Table 9 shows the AUC (area under the curve) from 0 to 9 hours for each sample.

TABLE 9

|  | Example 2 | L10 oil |
|---|---|---|
| $AUC_{0-9\ hr}$ (ng/mL)·hr | 345.0 ± 52.0 | 161.3 ± 66.4 |

The above has demonstrated that the emulsion composition of the present invention provides higher in vivo absorbability than oil itself or conventional emulsion compositions.

Example 5

Skin Lotion

<Composition>

| (1) 1,3-butanediol | 60 g |
|---|---|
| (2) Glycerin | 40 g |
| (3) Oleyl alcohol | 1 g |
| (4) Polyoxyethylene (20) sorbitan monolaurate | 5 g |
| (5) Polyoxyethylene (15) lauryl alcohol ether | 5 g |
| (6) Ethanol | 100 g |

| | |
|---|---|
| (7) Antiseptic | 2 g |
| (8) Sodium L-ascorbate | 10 g |
| (9) Emulsion composition of Example 1 | 776 g |
| (10) Purified water | Balance |

(1) was dissolved in (10) to form an aqueous phase. (2) to (5), (7), and (8) were added to and dissolved in (6) to form an oil phase. The oil phase and the aqueous phase were mixed and stirred, to which (9) was finally added, mixed, and stirred to form a skin lotion.

Example 6

Aqueous Beverage

<Composition>

| | |
|---|---|
| (1) Emulsion composition of Example 1 | 10 g |
| (2) Granulated sugar | 2 g |
| (3) Sodium chloride | 1 g |
| (4) Acidulant | Proper amount |
| (5) Sodium L-ascorbate | 0.5 g |
| (6) Ion-exchanged water | Balance (to a total of 100 g) |

These ingredients were mixed and stirred to form an aqueous beverage.

Example 7

Hard Capsule Preparation

The emulsion composition (50 g) prepared in Example 1 was encapsulated in Licaps size 1 (a hard capsule raw material manufacture by Capsugel) by a conventional technique, so that 100 hard capsules each containing 500 mg of the emulsion composition were prepared.

INDUSTRIAL APPLICABILITY

The present invention provides a stable emulsion composition of a lipophilic material, in which the lipophilic material, specifically, a carotenoid such as astaxanthin, has very high bioavailability. Therefore, the present invention makes it possible to impart high quality to food products, cosmetics, supplements, pharmaceuticals, and other products.

The invention claimed is:

1. An emulsion composition comprising
   (a) (a1) a *Haematococcus alga* extract comprising astaxanthins and an acyl glycerol comprising at least one of a monoglyceride, a diglyceride, and a triglyceride, and (a2) a fat or an oil comprising a C6-12 saturated medium fatty chain triglyceride,
   (b) lecithin,
   (c) glycerin,
   (d) water,
   (e) a sucrose monostearate, and
   (f) decaglycerol monolaurate, wherein
   (a-1a) the *Haematococcus alga* extract has an astaxanthins content of at least 9% by weight, and the weight ratio of the acyl glycerol to 1 part by weight of astaxanthin in the *Haematococcus alga* extract is from 2 to 8,
   (a-2a) the weight ratio of the triglyceride to 1 part by weight of the *Haematococcus alga* extract is from 0.2 to 1.5,
   (a-1b) the astaxanthins are present in an amount of 1.5 to 3.0 parts by weight to 100 parts by weight of the total of the emulsion composition,
   (b-1) the content of the (b) lecithin is from 2.5 to 5.5 parts to 100 parts by weight of the total of the emulsion composition,
   (c-1) the content of the (c) glycerin to 100 parts by weight of the total of the emulsion composition is from 30 to 65 parts,
   (d-1) the content of the (d) water to 100 parts by weight of the total of the emulsion composition is from 10 to 30 parts,
   (d-2) the weight ratio of (d) water to 1 part by weight of the astaxanthins is from 7 to 15 parts,
   (e-1) the content of the (e) sucrose monostearate to 100 parts by weight of the total of the emulsion composition is from 5 to 8 parts,
   (f-1) the content of the decaglycerol monolaurate to 100 parts by weight of the total of the emulsion composition is from 2 to 7 parts,
   (f-2) the weight ratio of the (f) decaglycerol monolaurate to 1 part by weight of the (e) sucrose monostearate is from 0.2 to 0.8,
   wherein the emulsion composition exhibits residual amount of astaxanthins in an amount 90.2% to 98.3% at 50° C. after 4 weeks of storage, wherein the emulsion composition is not separated immediately, and wherein the emulsion is not separated 4 weeks after preparation, and an average particle size of 104.7 nm to 118.4 nm.

2. The emulsion composition according to claim 1, wherein the weight ratio of the (b) lecithin to the astaxanthins is from 1.1 to 4.5 parts by weight of the (b) lecithin to 1 part by weight of the astaxanthin.

3. A food, pharmaceutical, and/or cosmetic product comprising the emulsion composition according to claim 1.

4. A hard or soft capsule preparation comprising the emulsion composition according to claim 1.

5. The emulsion composition according to claim 1, wherein the emulsion composition exhibits residual amount of astaxanthins in an amount of about 94% to about 98.3% at 50° C. after 4 weeks of storage and an average particle size of 118 nm to 111.3.

6. A method of preparing the emulsion composition according to claim 1, the method comprising: (1) mixing and dissolving sucrose monostearate, glycerin, and optionally a polyol in water to form an aqueous phase; (2) mixing and dissolving the *Haematococcus alga* extract, fat or oil, lecithin, the acyl glycerol, and decaglycerol monolaurate and a phospholipid, and optionally a polyol to form an oil phase; and (3) mixing the aqueous phase and the oil phase to yield the emulsion.

* * * * *